US011083719B2

(12) United States Patent
Magaña Castro et al.

(10) Patent No.: US 11,083,719 B2
(45) Date of Patent: *Aug. 10, 2021

(54) GEL CONTAINING PIRFENIDONE

(71) Applicant: Excalibur Pharmaceuticals, Inc., New York, NY (US)

(72) Inventors: José Agustín Rogelio Magaña Castro, Mexico City (MX); Laura Vázquez Cervantes, Mexico City (MX); Juan Socorro Armendáriz Borunda, Mexico City (MX)

(73) Assignee: Excalibur Pharmaceuticals, Inc., New York, NY (US)

( * ) Notice: Subject to any disclaimer, the term of this patent is extended or adjusted under 35 U.S.C. 154(b) by 20 days.

This patent is subject to a terminal disclaimer.

(21) Appl. No.: 16/450,150

(22) Filed: Jun. 24, 2019

(65) Prior Publication Data

US 2020/0016138 A1 Jan. 16, 2020

Related U.S. Application Data

(62) Division of application No. 15/435,494, filed on Feb. 17, 2017, now Pat. No. 10,376,500, which is a division of application No. 13/893,626, filed on May 14, 2013, now abandoned, which is a division of application No. 12/673,304, filed as application No. PCT/MX2008/000107 on Aug. 14, 2008, now Pat. No. 8,492,412.

(30) Foreign Application Priority Data

Aug. 14, 2007 (MX) .................. MX/A/2007/009796

(51) Int. Cl.
| | |
|---|---|
| A61K 31/4418 | (2006.01) |
| A61K 9/00 | (2006.01) |
| A61K 9/06 | (2006.01) |
| A61K 47/02 | (2006.01) |
| A61K 47/18 | (2017.01) |
| A61K 47/22 | (2006.01) |
| A61K 47/32 | (2006.01) |

(52) U.S. Cl.
CPC ........ *A61K 31/4418* (2013.01); *A61K 9/0014* (2013.01); *A61K 9/06* (2013.01); *A61K 47/02* (2013.01); *A61K 47/18* (2013.01); *A61K 47/22* (2013.01); *A61K 47/32* (2013.01)

(58) Field of Classification Search
CPC .... A61K 31/4418; A61K 47/18; A61K 47/22; A61K 9/0014; A61K 9/06
See application file for complete search history.

(56) References Cited

U.S. PATENT DOCUMENTS

| | | | |
|---|---|---|---|
| 4,105,782 A | 8/1978 | Yu et al. | |
| 4,376,118 A | 3/1983 | Daher et al. | |
| 5,009,895 A | 4/1991 | Lui | |
| 5,310,562 A * | 5/1994 | Margolin | A61K 31/44 424/423 |
| 5,811,130 A | 9/1998 | Boettner et al. | |
| 5,958,420 A | 9/1999 | Jenson | |
| 6,365,131 B1 | 4/2002 | Doshi et al. | |
| 7,109,246 B1 | 9/2006 | Hawtin | |
| 8,492,412 B2 | 7/2013 | Magana Castro et al. | |
| 9,408,836 B2 | 8/2016 | Armendariz Borunda et al. | |
| 9,949,959 B2 | 4/2018 | Armendariz Borunda et al. | |
| 9,962,374 B2 | 5/2018 | Armendariz Borunda et al. | |
| 10,383,862 B2 | 8/2019 | Armendariz Borunda et al. | |
| 10,792,258 B2 | 10/2020 | Magana Castro et al. | |
| 2004/0029946 A1 | 2/2004 | Arora et al. | |
| 2004/0235946 A1 | 11/2004 | Ott | |
| 2006/0039931 A1 | 2/2006 | Scheiwe et al. | |
| 2006/0051339 A1 | 3/2006 | Sivak | |
| 2006/0115503 A1 | 6/2006 | Goyal | |
| 2007/0128258 A1 * | 6/2007 | Faure | A61K 9/107 424/445 |
| 2008/0319026 A1 | 12/2008 | Gant et al. | |
| 2011/0224265 A1 | 9/2011 | Magana Castro et al. | |
| 2013/0245073 A1 | 9/2013 | Magana Castro et al. | |
| 2014/0296300 A1 | 10/2014 | Armendariz Borunda et al. | |
| 2015/0148382 A1 | 5/2015 | Armendariz Borunda et al. | |
| 2015/0231098 A1 | 8/2015 | Magana Castro et al. | |
| 2016/0228424 A1 | 8/2016 | Armendariz Borunda et al. | |
| 2016/0287567 A1 | 10/2016 | Armendariz Borunda et al. | |
| 2017/0216268 A1 | 8/2017 | Magana Castro et al. | |
| 2018/0092893 A1 | 4/2018 | Armendariz Borunda et al. | |
| 2018/0214434 A1 | 8/2018 | Armendariz Borunda et al. | |

(Continued)

FOREIGN PATENT DOCUMENTS

| | | |
|---|---|---|
| CN | 101 972 225 A | 2/2011 |
| CN | 101972236 A | 2/2011 |

(Continued)

OTHER PUBLICATIONS

U.S. Appl. No. 15/435,494, filed Feb. 17, 2017, Jose Agustin Rogelio Magaila Castro.
U.S. Appl. No. 13/893,626, filed May 14, 2013, Jose Agustin Rogelio Magaila Castro.
U.S. Appl. No. 12/673,304, filed Apr. 28, 2010, Jose Agustin Rogelio Magaila Castro.
U.S. Appl. No. 15/831,650, filed Dec. 5, 2017, Juan Socorro Armendáriz Borunda.
U.S. Appl. No. 15/177,760, filed Jun. 9, 2016, Juan Socorro Armendáriz Borunda.
U.S. Appl. No. 14/233,600, filed May 20, 2014, Juan Socorro Armendáriz Borunda.
U.S. Appl. No. 15/920,822, filed Mar. 14, 2018, Juan Socorro Armendáriz Borunda.

(Continued)

Primary Examiner — San Ming R Hui
(74) Attorney, Agent, or Firm — Wolf, Greenfield & Sacks, P.C.

(57) ABSTRACT

The invention relates to a gel composition containing pirfenidone, which is advantageous over other cutaneously administered pharmaceutical forms known in the prior art and which can be used in treatment for the restoration of tissues with fibrotic lesions and for the prevention of fibrotic lesions.

22 Claims, No Drawings

(56) References Cited

U.S. PATENT DOCUMENTS

| | | | |
|---|---|---|---|
| 2018/0353448 A1 | 12/2018 | Magana Castro et al. |
| 2019/0262325 A1 | 8/2019 | Armendariz Borunda et al. |
| 2019/0290606 A1 | 9/2019 | Magana Castro et al. |
| 2019/0358213 A1 | 11/2019 | Armendariz Borunda et al. |
| 2020/0016138 A1 | 1/2020 | Magana Castro et al. |
| 2020/0038386 A1 | 2/2020 | Armendariz Borunda et al. |
| 2020/0061040 A1 | 2/2020 | Armendariz Borunda et al. |
| 2020/0253944 A1 | 8/2020 | Magana Castro et al. |

FOREIGN PATENT DOCUMENTS

| | | | |
|---|---|---|---|
| EP | 1356816 A1 | 10/2003 |
| EP | 2177220 A1 | 4/2010 |
| EP | 2832354 A1 | 2/2015 |
| EP | 2907506 | 8/2015 |
| MX | 2013008151 A | 10/2013 |
| WO | WO 99/047140 A1 | 9/1999 |
| WO | 2000/16775 A1 | 3/2000 |
| WO | 2004/073713 A1 | 9/2004 |
| WO | WO 2005/000227 | 1/2005 |
| WO | 2007/038315 A2 | 4/2007 |
| WO | 2008107873 A1 | 9/2008 |
| WO | 2009/022899 A1 | 2/2009 |
| WO | 2013/012307 A1 | 1/2013 |
| WO | 2013/147577 A1 | 10/2013 |

OTHER PUBLICATIONS

U.S. Appl. No. 15/098,970, filed Apr. 14, 2016, Juan Socorro Armendáriz Borunda.
U.S. Appl. No. 14/388,447, filed Feb. 5, 2015, Juan Socorro Armendáriz Borunda.
U.S. Appl. No. 15/435,494, Apr. 3, 2019.
U.S. Appl. No. 15/435,494, Sep. 20, 2018.
U.S. Appl. No. 15/435,494, Jan. 26, 2018.
U.S. Appl. No. 15/435,494, Sep. 8, 2017.
U.S. Appl. No. 13/893,626, Aug. 22, 2016.
U.S. Appl. No. 13/893,626, Dec. 17, 2015.
U.S. Appl. No. 13/893,626, Apr. 14, 2015.
U.S. Appl. No. 12/673,304, Mar. 8, 2013.
U.S. Appl. No. 12/673,304, Jun. 20, 2012.
U.S. Appl. No. 12/673,304, Mar. 14, 2012.
U.S. Appl. No. 15/831,650, Jun. 26, 2019.
U.S. Appl. No. 15/831,650, Mar. 19, 2019.
U.S. Appl. No. 15/831,650, Oct. 2, 2018.
U.S. Appl. No. 15/831,650, Jun. 13, 2018.
U.S. Appl. No. 15/177,760, Nov. 2, 2017.
U.S. Appl. No. 15/177,760, Apr. 17, 2017.
U.S. Appl. No. 15/177,760, Dec. 15, 2016.
U.S. Appl. No. 14/233,600, May 20, 2016.
U.S. Appl. No. 14/233,600, Nov. 23, 2015.
U.S. Appl. No. 14/233,600, Jul. 8, 2015.
U.S. Appl. No. 15/920,822, Feb. 7, 2019.
U.S. Appl. No. 15/920,822, Nov. 15, 2018.
U.S. Appl. No. 15/098,970, Dec. 15, 2017.
U.S. Appl. No. 15/098,970, Mar. 23, 2017.
U.S. Appl. No. 15/098,970, Jan. 11, 2017.
U.S. Appl. No. 14/388,447, Oct. 15, 2015.
[No Author Listed] Understanding Acne Treatment, *WebMD*, Retrieved from https://www.Webmd.com/skin-problems-and-treatnnents/acne/understanding-acne-treatnnent#5 on Feb. 4, 2019. 5 pages.
Database WPI Section Ch, Week 200629 Thomson Scientific, London, GB; Class B03, AN 2006-273778, Wu J: Use of pirfenidone for treating hepatic injury and necrosis and acute lung injury, Shanghai Genomics) p. 7; (2005).
Database WPI Section Ch, Week 201139 Thomson Scientific, London, GB; Class A96, AN 2011-D92901, Li X: Sustained-release tablet comprises pirfenidone, substance capable of releasing active ingredient, and additive, Med Pharm Sci& Technology Co, 1 page (2011).
Database WPI Section Ch, Week 201427 Thomson Scientific, London, GB; Class A96, AN 2014-F77081, Deng C et al., "Pharmaceutical composition used for treating hepatic fibrosis, liver fibrosis, liver cirrhosis, and liver cancer comprises pirfenidone, inosine, and auxiliary materials", Sichuan Guokang Pharm Co Ltd, 1 page (2014).
Garcia et al., Pirfenidone effectively reverses experimental liver fibrosis. J Hepatol. Dec. 2002;37(6):797-805.
Macias-Barragan J, et al., 5-Methyl-1-Phenyl-2-(1H)-Pyridone Treatment Improves Markers of Hepatic Function and Fibrosis in Steatosis Included by High Fat/Carbohydrate Diet, Journal of Hepatology, Abstract of the International River Congress™ 2014—49th Annual Meeting of the European Association for the Study of the Liver, Abstract P428, vol. 60(1)Suppl.1: S210 (2014).
Macias-Barragan, J. et al., "Pirfenidone LP activates PPARalpha and LXRalpha and results in decreased expression of proinflammatory cytokines and improvement of NASH features induced by high fat/carbohydrate diet," Hepatology—Special Issue: The 67th Annual Meeting of the American Association for the Study of Liver Diseases: The Liver Meeting 2016, Abstract No. 1541: vol. 64(SI): 767A-768A: 2 pages (2016).
Nakanishi, H. et al., Pirfenidone inhibits the induction of iNOS stimulated by interleukin-1beta at a step of NF-kappaE DNA binding in hepatocytes. J Hepatology, vol. 41(5):730-736 (2004).
Ozes et al., Preclinical activity of pirfenidone (5-methyl-1phenyl-2 (IH)-pyridone) in cell-based models of Nonalcoholic steatohepatitis. Hepatology, Abstract 697, 2003;34(4): 495A.
Veras-Castillo et al., Controlled clinical trial with pirfenidone in the treatment of breast capsular contracture: Association of TGF polymorphisms. Annals Plastic Surgery. 2013;70(1):16-22.
U.S. Appl. No. 14/233,600, filed May 20, 2014, Armendáriz Borunda et al.
U.S. Appl. No. 15/177,760, filed Jun. 9, 2016, Armendáriz Borunda et al.
U.S. Appl. No. 15/831,650, filed Dec. 5, 2017m Armendáriz Borunda et al.
U.S. Appl. No. 16/544,643, filed Aug. 19, 2019, Armendáriz Borunda et al.
U.S. Appl. No. 16/460,407, filed Jul. 2, 2019, Armendáriz Borunda et al.
U.S. Appl. No. 12/673,304, filed Apr. 28, 2010, Magaña Castro et al.
U.S. Appl. No. 13/893,626, filed May 14, 2013, Magaña Castro et al.
U.S. Appl. No. 15/435,494, filed Feb. 17, 2017, Magaña Castro et al.
Allicinnow, "allicin," retrieved online at: http://www.allicinnow.com/allicin/acne-treatmentl, 2 pages (2010).
Armendariz-Borunda, Juan et al., "A Controlled Clinical Trial With Pirfenidone in the Treatment of Pathological Skin Scarring Caused by Burns in Pediatric Patients," Annals of Plastic Surgery, vol. 68(1):22-28 (2012).
Gad, C.G., "Pharmaceutical Manufacturing Handbook: production and processes," John Wiley & Sons, ISBN: 978-0-470-25958-0, 1386 pages (Mar. 2008).
International Preliminary Report on Patentability for Application No. PCT/MX2008/000107, 11 pages, dated Dec. 1, 2009.
International Preliminary Report on Patentability for Application No. PCT/MX2012/000067, 8 pages, dated Aug. 7, 2013.
International Preliminary Report on Patentability, for Application No. PCT/MX2013/000099, dated Dec. 19, 2014, 7 pages.
International Search Report and Written Opinion for Application No. PCT/MX2012/000067, dated Nov. 22, 2012, 12 pages.
International Search Report and Written Opinion for Application No. PCT/MX2013/000027, dated Jun. 5, 2013, 11 pages.
International Search Report and Written Opinion, PCT/MX2013/000099, dated Aug. 8, 2014, 9 pages.
International Search Report for Application No. PCT/MX2008/000107, dated Dec. 9, 2008, 3 pages.
Josling, Peter, "Peter Josling's PowerPoint on AllicinCenter Products and Their Uses," retrieved from the internet at: http://allicincenter.com/reference.php?id=products, 15 pages (2013).

(56) References Cited

OTHER PUBLICATIONS

Tiwari, S., et al., "Applications of Complementary Polymers in HPMC Hydrophilic Extended Release Matrices," Drug Delivery Technology, Formulating Hydrophilic Matrix Systems, vol. 9(7), 7 pages (2009).
U.S. Appl. No. 17/063,458, filed Oct. 5, 2020, Magana Castro et al.
PCT/MX2017/000129, Jan. 28, 2018, International Preliminary Report on Patentability.
PCT/MX2017/000129, Apr. 9, 2018, International Search Report and Written Opinion.
PCT/MX2018/000071, Mar. 28, 2019, International Search Report and Written Opinion.
PCT/MX2018/000071, Jul. 19, 2019, International Preliminary Report on Patentability.
PCT/MX2019/000093, Aug. 4, 2020, Translation of the International Search Report and Written Opinion.
International Preliminary Report on Patentability, dated Jan. 28, 2018 for Application No. PCT/MX2017/000129.
International Search Report and Written Opinion, dated Apr. 9, 2018 for Application No. PCT/MX2017/000129.
International Search Report and Written Opinion, for Application No. PCT/MX2018/000071, dated Mar. 28, 2019.
International Preliminary Report on Patentability, for Application No. PCT/MX2018/000071, dated Jul. 19, 2019.
International Search Report and Written Opinion, for Application No. PCT/MX2019/000093, dated Aug. 4, 2020.
Ojeda-Duran et al., Evaluation of Safety of a Newly Formulated Pirfenidone in Chronic Kidney Disease: A Non-Randomized Pilot Study in Mexican Patients. J Renal Hepatic Disorders. 2020;4(1):22-30.
Park et al., Pirfenidone suppressed the development of glomerulosclerosis in the FGS/Kist mouse. J Korean Med Sci. Aug. 2003;18(4):527-33.

* cited by examiner

GEL CONTAINING PIRFENIDONE

RELATED APPLICATIONS

This application is a divisional application of U.S. patent application Ser. No. 15/435,494 (allowed), filed on Feb. 17, 2017, which is a divisional application of U.S. patent application Ser. No. 13/893,626, filed on May 14, 2013, which is a divisional application of U.S. patent application Ser. No. 12/673,304, filed on Apr. 28, 2010 (now U.S. Pat. No. 8,492,412), which claims the benefit of and which is a national stage filing of International Application Serial No. PCT/MX2008/000107, filed on Aug. 14, 2008, which claims priority to, and the benefit of, Mexican Patent Application Serial No. MX/a/2007/009796, filed on Aug. 14, 2007, the entire contents of both of which are hereby incorporated by reference.

FIELD OF INVENTION

The present invention is related to a gel formula that contains Pirfenidone, which offers advantages over other pharmaceutical forms of known cutaneous administration in the state of the technique.

BACKGROUND OF THE INVENTION

The 5-methyl-1-phenyl-2(1H)-pyridone, formula;

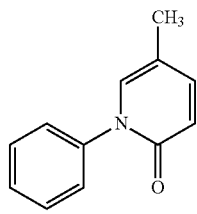

It is a drug that has been applied in the restoration of tissues with lesions with fibrosis and the prevention of fibrotic lesions. This compound, Pirfenidone, it is by itself a known compound and its pharmacological effects has been described, for example, in Japanese applications numbers 87677/1974 and 1284338/1976, as an anti-inflammatory agent that includes antipyretic and analgesics. The U.S. Pat. No. 3,839,346, published Oct. 1, of 1974; the U.S. Pat. No. 3,974,281, published Aug. 10, of 1976; the U.S. Pat. No. 4,042,699 published Aug. 16, of 1977, and the U.S. Pat. No. 4,052,509 published Oct. 4, of 1977, which described the methods for the obtained Pirfenidone, as well as its use as an anti-inflammatory agent. In the Mexican patent 182, 266 the antifibrotic activity of the 5-methyl-1-phenyl-2(1H)-pyridone is described.

Different resources and treatments have been used to the date and none of them have shown to be really effective. Pirfenidone has shown its efficacy as an anti-fibrotic agent in different pathologies and organs, and has been demonstrated in previous works, where we have observed an effect on the fibroblasts and the production of collagen and extracellular matrix, as well as in experimental models and in clinical tests also.

Many substances could form gels when a gelificant agent is added. This is use in many diverse products in the manufacturing industry, from food to paint, passing through adhesives.

Gels are also important in the chemistry part related with the processes SOL_GEL and in the synthesis of solid materials with nanopores.

Gels are classified in: aqueous (hydrogels) or organic (organogels), dependingo if the aqueous component is water or an organic solvent; organic or inorganic in nature, colloidal or thick grain, according to the size of the particles; and rigid gels, elastic or tixothrophic, according to its mechanic properties.

The hydrocolloids are substances that are produced from vegetable and animal proteins or multiple sugars. They have the capacity to swell themselves and to bind to water. The hydrocolloids are used to thicken, solidify and stabilize food.

OBJECT OF THE INVENTION

The object of the present invention is to provide a gel composition for its cutaneous administration that contains Pirfenidone, a viscous agent; a solubilizer; a non ionic solubilizer; a conserving agent; a neutralizer agent and purified water.

Also, it is the object of the present invention to provide a process of manufacture of a gel that contains pirfenidone for its cutaneous application.

Another objective of the present invention is to provide a gel medicine to be used as an anti-fibrotic and anti-inflammatory agent.

SPECIFICATION OF THE INVENTION

Composition of the Gel

The composition of the gel contains from 2 to 12% of Pirfenidone is elaborated utilizing from 0.4 to 1.2% of a viscous agent, from 10 to 30% of a solubilizer, from 5 to 15% of a non ionic solubilizer, from 0.2 to 1% of a conserving agent, from 0.4 to 1.2% a neutralizer agent and the rest of purify water. The viscous agent is selected from a carbomer 940 (MR); Ultrex 10(MR), cellulose derivatives; gums; polioxameres; ethylic alcohol and propylenglycol; the conserving agent is selected from a group that consist of Diazolidinyl urea, iodopropinil-butilcarbamate; methylparabene and a mix of these compounds; the neutralizer agent is selected from a group of primary, secondary and tertiary aliphatic amines of the mono- , bi- and triethanolamine type, and of the hydroxide alkaline metals, such as sodium hydroxide.

An example of the composition of the gel is shown in the table 1:

| Component | Quantity (g) | % |
| --- | --- | --- |
| Pirfenidone | 8 | 8 |
| Viscous agent | 0.5 | 0.5 |
| Solubilizer | 20 | 20 |
| Non ionic solubilizer | 11.5 | 11.5 |
| Conserving agent | 0.5 | 0.5 |
| Neutralizer | 0.5 | 0.5 |
| Purified water up to | 100 | 59 |

The gel containing Pirfenidone is manufactured as follows:
 a) Mix 50% of the total water to be used with the viscous agent, allowing the complete humectation of the viscous agent;
 b) Mix separately and with constant agitation the Pirfenidone with the solubilizer agent;

c) Dissolve separately the non ionic solubilizer agent in the 25% water to be used at 40° C., once dissolved, the 15% of the total water is added;
d) Add the solution from part c) to the mix from part b), agitate until the mix is homogenate.
e) Dilute the neutralizer agent in 10% of the total water to use, agitate until the mix is homogenate; and
f) Add with constant agitation and homogenate in each addition to the mix from part a) the solution from part d); the conservative and the solution from part e).

A prepared composition according to procedure describe is shown in table 2.

| Component | Quantity (g) |
| --- | --- |
| Pirfenidone | 8 |
| Carbomer | 0.5 |
| N-methylpirrolidone | 20 |
| Macrogolglycerol Hidroxiestearate 40 | 11.5 |
| Diazolidinilurea and Iodopropinil-butilcarbamate | 0.5 |
| Triethanoalamine | 0.5 |
| Purified water up to | 100 |

These compositions are shown in an example mode, but they are not limited in any level of the reach of the description of the present invention.

The invention claimed is:

1. A method for treating fibrotic lesions in a patient by administering to the patient a composition of pirfenidone gel consisting of:
   (a) 2-12% pirfenidone;
   (b) 0.4-1.2% of a viscous agent selected from the group consisting of Carbomer 940, Ultrex 10, cellulose derivatives, gums, and poloxamers;
   (c) 10-30% of a solubilizer selected from the group consisting of N-methylpyrrolidone, ethyl alcohol, and propylene glycol;
   (d) 5-15% of a non-ionic solubilizer;
   (e) 0.2-1% of a conserving agent selected from the group consisting of diazolidinyl urea, iodopropynyl butylcarbamate, methylparaben, propylparaben, and combinations of these conserving agents;
   (f) 0.4-1.2% of a neutralizer agent selected from the group consisting of primary, secondary and tertiary mono-, bi-, and triethanolamine aliphatic amines, and hydroxide alkaline metals; and
   (g) water;
   thereby treating the fibrotic lesions.

2. The method of claim 1, wherein the composition is prepared by:
   (a) mixing approximately 50% of the total water to be used with the viscous agent and allowing complete humectation of the viscous agent;
   (b) mixing pirfenidone and the solubilizer separately and with agitation;
   (c) dissolving separately the non-ionic solubilizer in approximately 25% of total water at approximately 40° C. and once dissolved, adding approximately 15% of the total water;
   (d) adding the solution from part (c) to the mix from part (b), and agitating until homogenous;
   (e) diluting the neutralizer agent in approximately 10% of the total water to be used, and agitating until homogenous; and
   (f) combining the solutions of parts (a)-(e).

3. The method of claim 1, wherein the conserving agent is a combination of diazolidinyl urea and iodopropynyl butylcarbamate.

4. The method of claim 1, wherein the viscous agent is Carbomer 940, the solubilizer is N-methylpyrrolidone, the conserving agent is diazolidinyl urea, and the neutralizer agent is triethanolamine.

5. The method of claim 1, wherein the viscous agent is Carbomer 940, the solubilizer is N-methylpyrrolidone, the conserving agent is iodopropynyl butylcarbamate, and the neutralizer agent is triethanolamine.

6. The method of claim 1, wherein at least one of the hydroxide alkaline metals is sodium hydroxide.

7. The method of claim 1, wherein the viscous agent is Carbomer 940.

8. The method of claim 1, wherein the viscous agent is Ultrex 10.

9. The method of claim 1, wherein the solubilizer is N-methylpyrrolidone.

10. The method of claim 1, wherein the solubilizer is propylene glycol.

11. The method of claim 1, wherein the conserving agent is diazolidinyl urea.

12. The method of claim 1, wherein the conserving agent is iodopropynyl butylcarbamate.

13. The method of claim 1, wherein the conserving agent is methylparaben.

14. The method of claim 1, wherein the conserving agent is propylparaben.

15. The method of claim 1, wherein the neutralizer agent is triethanolamine.

16. The method of claim 1, wherein the neutralizer agent is hydroxide alkaline metal.

17. The method of claim 1, wherein the non-ionic solubilizer is macrogolglycerol hydroxystearate 40.

18. The method of claim 1, wherein the method causes restoration of tissue with fibrotic lesions.

19. The method of claim 1, wherein the composition of pirfenidone gel consists of 8% pirfenidone, 0.5% of the viscous agent, 20% of the solubilizer, 11.5% of the non-ionic solubilizer, 0.5% of the conserving agent, 0.5% of the neutralizer agent, and 59% of purified water.

20. The method of claim 1, wherein the viscous agent is Carbomer 940, the solubilizer is N-methylpyrrolidone, the conserving agent is diazolidinyl urea and iodopropynyl butylcarbamate, and the neutralizer agent is triethanolamine.

21. The method of claim 1, wherein the neutralizer agent is sodium hydroxide.

22. The method of claim 1, wherein the administering comprises cutaneous administration.

* * * * *